United States Patent [19]

Wanderer et al.

[11] Patent Number: 4,693,708
[45] Date of Patent: Sep. 15, 1987

[54] COMBINATION NEEDLE SHIELD/NEEDLE GUARD DEVICE FOR A HYPODERMIC SYRINGE WITH A PERMANENTLY ATTACHED NEEDLE

[76] Inventors: Alan A. Wanderer, 1075 E. Radcliffe, Englewood, Colo. 80110; William E. Sagstetter, 2217 Grove, Denver, Colo. 80210

[21] Appl. No.: 919,373

[22] Filed: Oct. 16, 1986

[51] Int. Cl.⁴ .............................................. A61M 5/32
[52] U.S. Cl. .................................... 604/198; 604/263
[58] Field of Search ............... 604/192, 187, 197, 198, 604/263

[56] References Cited

U.S. PATENT DOCUMENTS

| | | | |
|---|---|---|---|
| 3,889,673 | 6/1975 | Dovey et al. | 604/192 |
| 4,425,120 | 1/1984 | Sampson et al. | 604/198 |
| 4,573,976 | 3/1986 | Sampson et al. | 604/198 |
| 4,592,745 | 6/1986 | Rex et al. | 604/192 |

Primary Examiner—John D. Yasko
Attorney, Agent, or Firm—Cahill, Sutton & Thomas

[57] ABSTRACT

This invention relates to a combination needle shield/needle guard device for a hypodermic syringe with a needle permanently attached to the front end of the syringe barrel. This needle shield/needle guard device is positively locked to the syringe barrel and can perform two functions: first, function as a needle shield which encloses and prevents contamination of a sterile needle and secondly, function as a needle guard which can slide on the surface of the syringe barrel, such that the needle can be uncovered and re-covered from behind the needle point, thereby providing a safety feature in that medical personnel can avoid direct contact with a needle point during the process of uncovering or re-covering the needle. More particularly, an unused sterile hypodermic needle is enclosed within the needle shield/needle guard device which protects the needle from contamination. Exteriorization of the needle from inside the needle shield/needle guard device occurs after an aperture is created by pulling off a tab at the front end of the needle shield/needle guard device and then retracting the needle shield/needle guard device on the syringe barrel, permitting the needle to exteriorize through the aperture. After the needle has been used for a medical procedure, extending the needle shield/needle guard device on the syringe barrel permits re-coverage of the used needle from behind the needle point, so that medical personnel avoid direct contact with the pointed end of a contaminated needle.

9 Claims, 14 Drawing Figures

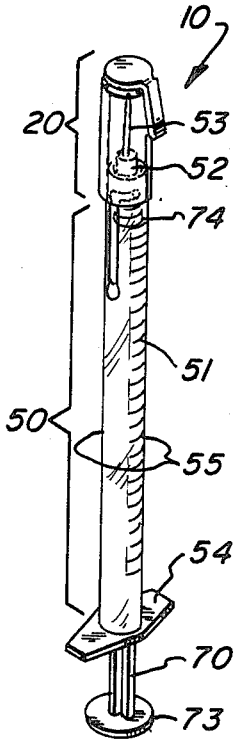
Fig_1
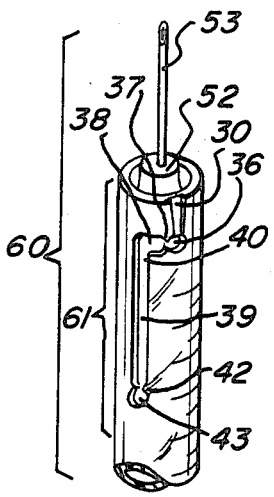
Fig_2
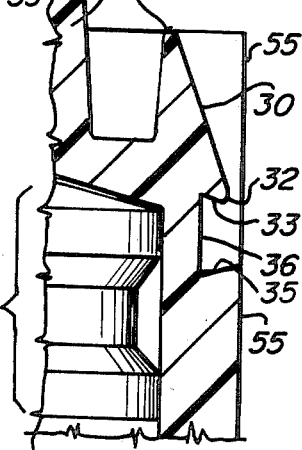
Fig_3
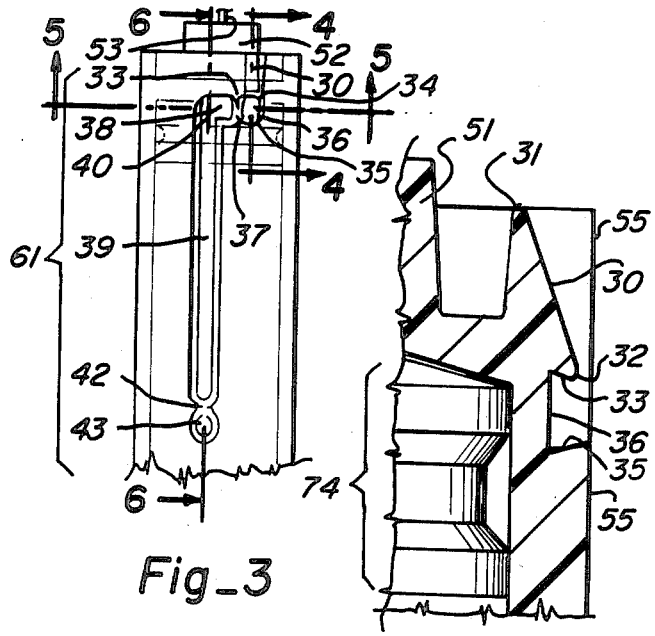
Fig_4
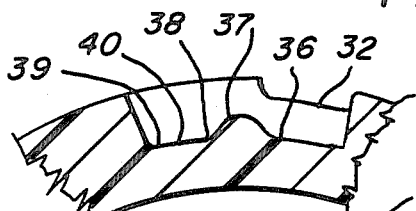
Fig_5
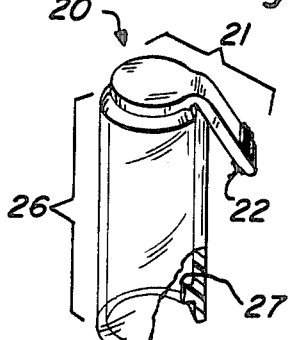
Fig_7
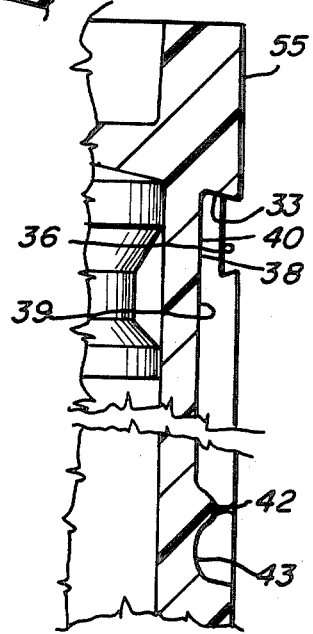
Fig_6

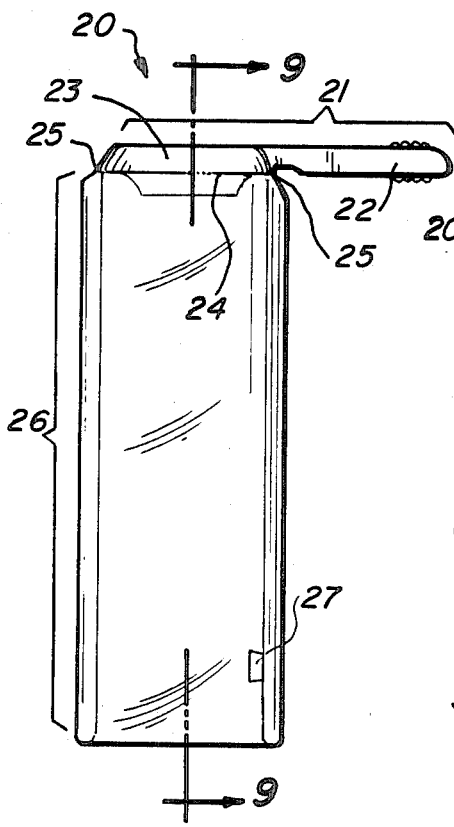
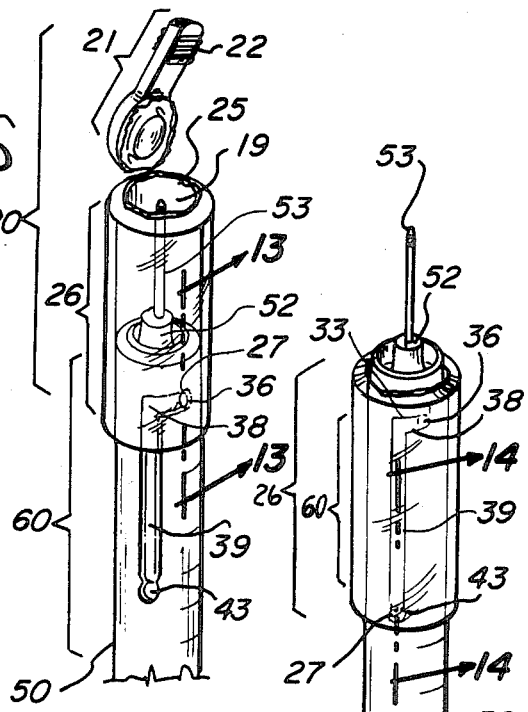
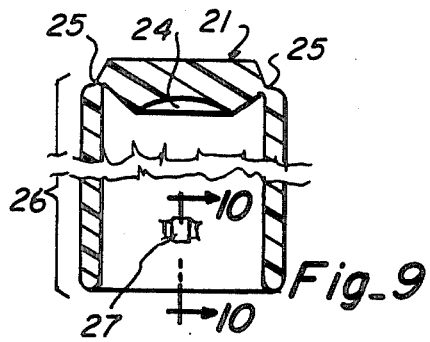
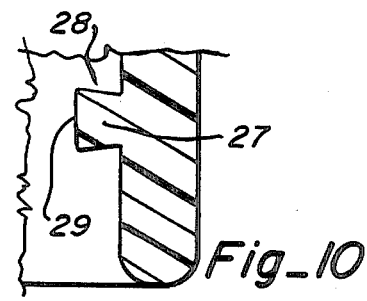
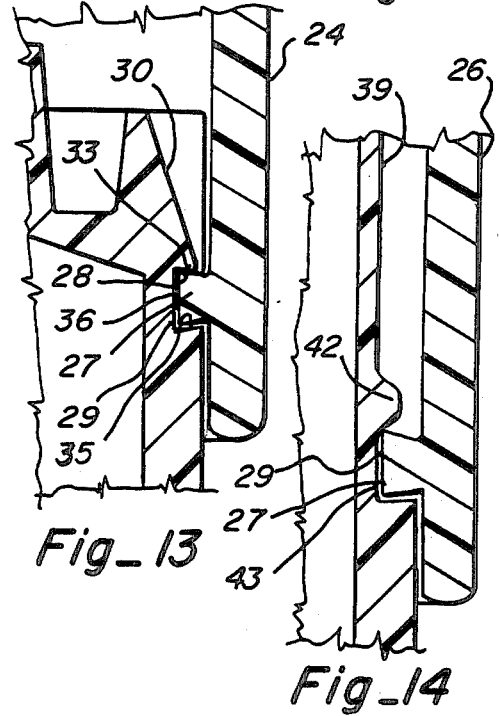
Fig_8  Fig_11  Fig_12
Fig_9
Fig_10
Fig_13  Fig_14

COMBINATION NEEDLE SHIELD/NEEDLE GUARD DEVICE FOR A HYPODERMIC SYRINGE WITH A PERMANENTLY ATTACHED NEEDLE

BACKGROUND OF THE INVENTION

1. Field of the Invention

This invention relates to a needle shield/needle guard device for a hypodermic syringe with a needle that is permanently attached to the forward end of the syringe barrel. This needle shield/needle guard device is positively locked to the syringe barrel and can perform two functions: (1) in the untampered state, it can function as a needle shield to enclose and prevent contamination of a sterile needle that is permanently attached to the forward end of the syringe barrel and, (2) after an aperture has been created by pulling off a tab on the front end of the device, it can function as a needle guard which permits the operator to uncover and re-cover a needle by retracting or extending the device on the syringe barrel from behind the needle point. The operator of this device can avoid direct contact with the needle point and thus reduce accidental puncture with used needles, which could transmit blood-borne infections such as AIDS, hepatitis, syphilis, and other infectious illnesses.

2. Description of the Prior Art

There are several major problems inherent in the design of existing needle shields which must be removed from needle hubs before a syringe needle can be used for a medical procedure. Examples of these removeable needle shields include the following references selected from the U.S. Patent and Trademark Office: U.S. Pat. Nos. 3,381,813; 3,934,722; 4,113,090; and 4,121,588. These removeable needle shields reveal several limitations such as: (1) after a liquid medicament has been drawn up in a syringe, medical personnel may occasionally delay the administration of the medicament, which would require replacement of a needle shield back over the needle to prevent contamination of the sterile needle. This maneuver requires keeping track of the removed needle shield and then replacing the needle shield back over the needle, which represent extra steps for busy medical personnel; (2) another common practice occurs when medical personnel remove this type of needle shield by holding the needle shield between their teeth or lips. This maneuver has been associated with accidental self-puncture in the face or other bodily parts; (3) in order to re-cover a used needle with a previously removed needle shield, it is necessary to replace the needle shield back over the pointed end of the used needle, which increases the risk to medical personnel who may accidentally puncture themselves with the pointed end of the used needle; (4) when the needle shield is replaced over the used needle, if the needle has been accidentally bent during a medical procedure or if the needle shield is replaced over the needle at an incorrect angle, the needle point may inadvertently pierce the side of the needle shield as it is being replaced over the needle. The operator using the needle shield could be punctured with a used needle point that has exteriorized through a needle shield; and (5) most medical facilities use storage containers with or without a clip-off needle device to store used needles. Personnel may puncture themselves with used, uncovered needles that may accidentally fall out of these storage containers or with uncovered needles that are disposed of inappropriately in wastebackets. In addition, if the storage container is full, it is possible to accidentally puncture oneself with a used, uncovered needle that is pointed towards the opening of the waste container.

Other devices relevant to the field of our invention are known and the following patents listed in the U.S. Patent and Trademark Office exhibit certain differences and/or limitations in comparison to our invention.

U.S. Pat. No. 4,425,120 issued to Sampson et al describes a needle guard device which is attached to a syringe barrel and functions to uncover or re-cover a needle. In this patent, in order to remove the detachable needle from the syringe barrel, it is necessary to recover the used needle with a separate needle shield, which increases the risk of puncture with a used needle point. In addition, this needle guard has an open-end, which precludes its use to function also as a needle shield to enclose and prevent contamination of a sterile needle. In order to prevent contamination of the sterile needle in this device, it would be necessary to cover the needle with a separate needle shield, or close the opening of the needle guard with a material which must be ruptured by the needle or needle shield enclosing the needle.

U.S. Pat. No. 4,139,009 issued to Alvarez is composed of four longitudinal arms which are brought into lateral side-to-side contact with the intention of covering and protecting the enclosed needle. The front end of the cover and the lateral arms in side-to-side contact represent discontinuous locations which could permit microorganism penetration and contamination of the enclosed sterile needle. In addition, the arms in their normal unstressed condition are slightly bowed away from the longitudinal axis of the needle, so that casual touching of the device could contaminate the needle through the open interspaces between the separated arms. When this device is pushed against a skin surface during the injection process, the arms must bow away from the longitudinal axis of the needle which could block visualization of the needle as it penetrates the skin. There are several medical indications in which the operator must observe the penetration of the needle into the skin in order o avoid a blood vessel or conversely, if the operator is attempting to withdraw blood it is important to be able to clearly visualize a blood vessel.

SUMMARY

This needle shield/needle guard device comprises a hollow translucent cylindrical housing which is closed off at its proximal end by an integral pull-off tab. The needle shield/needle guard is positively locked onto the front end of a syringe barrel where it encloses a sterile needle which is permanently attached to a hypodermic syringe barrel. In this capacity, the needle shield/needle guard device functions as a needle shield, which protects and prevents contamination of the enclosed sterile needle. The enclosed needle is exteriorized by first creating an aperture on the proximal end of the cylindrical housing. This occurs by pulling off an integral tab attached to the annular weakened zone on the cylindrical housing. The cylindrical housing of the needle shield/needle guard device is positively locked onto the front end of the syringe barrel. This occurs by the engagement of an internal protrusion (i.e. extends on the distal inner diameter of the cylindrical housing) into grooves located on the front end of the syringe barrel. The cylindrical housing with the pull-off tab removed can then function as a moveable needle guard, such that the operator can uncover the sterile needle and then recover the used needle in a direction which is always behind the needle point. In order to function as a needle guard, the operator must first remove the pull-off tab, and then move the cylindrical housing along grooves on the syringe barrel until the cylindrical housing is locked into the retracted lock position, thereby uncovering the sterile needle. After the needle has been used, the cylindrical housing can then be moved in a reverse direction so that it can be locked back into the extended lock position on the front end of the syringe barrel, thereby re-covering the used needle. These maneuvers allow the operator to avoid direct contact with the used needle point, which reduces the hazard of self-puncture and the associated risk of contracting blood-borne infections, such as AIDS, infectious hepatitis, syphilis, etc.

In accordance with the principles of the present invention, there are structural elements and features herein which are notably different from prior inventions of this type. First, this device has been developed to serve two distinct functions: (1) function as a needle shield to enclose and prevent contamination of the sterile needle permanently attached to the hypodermic syringe and (2) function as a moveable needle guard on the syringe barrel which is capable of protecting users such as medical personnel and patients (i.e. diabetics, allergy patients, etc. who self-administer injections of liquid medicaments) from puncturing themselves with contaminated needle points, since the needle point can be re-covered by moving the device from behind the needle point. It is important to emphasize that our device would provide a distinct advantage over prior art which includes devices that serve only one of these aforementioned functions. In addition, manufacturing costs should be reduced with our device since it requires only one part to perform both functions (i.e. needle shield and needle guard).

Secondly, our device can improve upon prior patented art in terms of the method of exteriorizing the needle from the device. In our device, an aperture is created at the front end of the device by removing a pull-off tab from an annular weakened zone on the cylindrical housing, which allows the needle point to exteriorize through the aperture in the needle shield/needle guard device without contacting any parts of the device. This method of needle exteriorization in our device precludes: (1) contact contamination of the needle point with other parts of the device; (2) the possibility of plugging or obstructing the needle point with foreign paticles since the needle does not exteriorize through a material; and (3) bending of the needle as it exteriorizes through the device since the needle does not exteriorize through a material. In addition, manufacturing costs could be replaced with our device which utilizes a pull-off tab as an integral part of the cylindrical housing, thereby requiring one material for the manufacture of the entire needle shield/needle guard device.

Thirdly, our device can assist medical personnel, who may need to delay the administration of a liquid medicament that has been drawn up in a hypodermic syringe. This need can be facilitated by moving an easily accessible, non-removeable needle shield/needle guard device back over the hypodermic needle to prevent contamination of the unused needle.

Fourth, our needle shield/needle guard device is positively locked onto the syringe barrel so that the operator can easily keep track of the device to re-cover used, blood contaminated needles, such that when used needles are disposed of in containers they will always be re-covered with the needle shield/needle guard device. The entire needle shield/needle guard device with the enclosed needle and attached syringe can be disposed of together. The operator also has the option of clipping the syringe barrel to separate off the needle shield/needle guard device with the enclosed needle. These features will reduce the risk of blood-borne infections to personnel handling the disposal of stored used needles since these needles will be covered with the needle shield/needle guard device.

Finally, in the preferred embodiment of our invention, the cylindrical housing is translucent so that the volumetric calibrations on the syringe barrel can be easily read by the user when the cylindrical housing is retracted over the volumetric calibrations on the syringe barrel.

Other objectives and advantages of our invention will become apparent more fully from the following description and accompanying drawings illustrating the device.

BRIEF DESCRIPTION OF THE DRAWINGS

FIG. 1 is an isometric view of a hypodermic syringe with needle shield/needle guard device attached to front end of syringe barrel.

FIG. 2 is an isometric view of front end of syringe barrel without attachment of needle shield/needle guard device.

FIG. 3 is an enlarged side view of front end section of syringe barrel illustrating the groove system.

FIG. 4 is a partial section of front end of syringe barrel along longitudinal plane (line 4—4 in FIG. 3).

FIG. 5 is a cross-sectional view along (line 5—5 in FIG. 3).

FIG. 6 is a partial section of front end of syringe barrel along longitudinal plane (line 6—6 in FIG. 3).

FIG. 7 is an isometric view of the needle shield/needle guard device with a broken away view of the internal protrusion.

FIG. 8 is a side view of needle shield/needle guard device with pull-off tab and handle.

FIG. 9 is a partial sectional view of needle shield/needle guard device along longitudinal plane (line 9—9 in FIG. 8).

FIG. 10 is a sectional view along longitudinal plane (line 10—10 in FIG. 9).

FIG. 11 is a partial isometric view of hypodermic syringe with attached needle shield/needle guard device after pull-off tab has been removed, illustrating needle shield/needle guard device in extended lock position on front end of syringe barrel.

FIG. 12 is a view similar to FIG. 11 illustrating the needle shield/needle guard device in retracted lock position on front end of syringe barrel.

FIG. 13 is a partial sectional view along longitudinal plane (line 13—13 of FIG. 11).

FIG. 14 is a partial sectional view along longitudinal plane (line 14—14 of FIG. 12).

DETAILED DESCRIPTION OF THE INVENTION

Referring to the drawings, a hypodermic syringe 10 is illustrated in FIG. 1 which comprises the needle shield/needle guard device 20, hollow cylindrical syringe barrel 50 with volumetric calibrations 51, external diameter of syringe barrel 55, needle hub 52 which is an integral part of the front end of the syringe barrel 50, needle 53 which is permanently secured along longitudinal axis to needle hub 52, wings 54 for ease of manual handling, and a plunger 70 with flattened outer end 73 and a piston 74 at the inner end of plunger 70 which slides inside syringe barrel 50.

Referring to FIG. 2, the front end 60 of the syringe barrel is comprised of the needle 53 which is permanently attached to the needle hub 52, and groove system 61 comprising a funneled lead-in sloping groove 30, extended lock position 36, constricting bead of the horizontal groove 37, the horizontal groove 38, the junction 40 joining the horizontal groove 38 and the longitudinal groove 39, the longitudinal groove 39, the constricting bead of the longitudinal groove 42, and the retracted lock position 43. FIG. 3 is an enlargement of the groove system 61 on the front end 60 of the syringe barrel 50. From this view, the funneled lead-in sloping groove 30 appears as a progressively narrowed pathway which joins to the extended lock position 36. The extended lock position 36 is divided from the horizontal groove 38 by the constricting bead of the horizontal groove 37. The horizontal groove 38 interconnects at the junction 40 with the longitudinal groove 39. At the distal end of the longitudinal groove 39, the constricting bead of the longitudinal groove 42 separates the longitudinal groove 39 from the retracted lock position 43.

Referring to FIG. 4, the funneled lead-in sloping groove 30 is shown at its proximal end 31 which is recessed below the external diameter of the syringe barrel 55 and slopes outwardly and distally towards the external diameter of the syringe barrel 55. The maximum outward extension of the sloping groove 32 then joins the retaining wall 33 of the funneled lead-in sloping groove 30 which then forms an acute angle with the extended lock position 36. The retaining wall 33 of the funneled lead-in sloping groove extends horizontally to become the front edge of the horizontal groove 38 (see also FIG. 3). The retaining walls 34 and 35 (FIG. 3) also form acute angles with the extended lock position 36 so when the internal protrusion 27 of the needle shield/needle guard device 20 is attached to the front end 60 of the syringe barrel (see FIGS. 11 and 13), the retaining walls 33, 34, and 35 provide forward, counterclockwise and backward positive locks respectively for the internal protrusion 27 in relation to the front end 60 of the syringe barrel.

Referring to FIG. 5, this cross-sectional view reveals the maximum outward extension of the funneled lead-in sloping groove 32, the extended lock position 36 which is separated off from the horizontal groove 38 by the constricting bead of the horizontal groove 37 shown as a rounded mound. The horizontal groove 38 interconnects at the junction 40 with the longitudinal groove 39.

Referring to FIG. 6, this longitudinal perspective reveals the retaining wall 33 of the sloping groove 30, the constricting bead of the horizontal groove 36, the horizontal groove 38 interconnecting with the longitudinal groove 39 at the junction 40. The drawing illustrates the constricting bead of the longitudinal groove 42 shown as a rounded mound which separates the longitudinal groove 39 from the retractedd lock position 43.

Referring to FIG. 7, the needle shield/needle guard device 20 is shown comprised of a pull-off tab 21 with its pull-off handle 22, and the hollow cylindrical housing 26. A break-away view of the distal inner wall of the cylindrical housing 26 reveals the internal protrustion 27. The needle shield/needle guard device 20 is constructed of a translucent material. FIG. 8 is a side view of the needle shield/needle guard device 20 revealing the pull-off tab 21, the top of the pull-off tab 23, the bottom of the pull-off tab 24, the pull-off tab handle 22, the annular weakened zone 25 where the pull-off tab is integrally attached to the cylindrical housing 26, and the internal protrusion 27.

Referring to FIG. 9, the annular weakened zone 25 of attachment of the pull-off tab 21 to the cylindrical housing 26 is illustrated. The internal protrusion 27 is also shown on the inner distal wall of the cylindrical housing 26. FIG. 10 is a longitudinal perspective of the internal protrusion 27 with its front wall 28 and bottom end 29. The internal protrusion 27 is shaped to fit complementarily into the extended lock position 36 within the retaining walals 33, 34 and 35 (see FIGS. 3 and 4).

FIGS. (11 to 14) illustrate the relationships between the needle shield/needle guard device 20, the pull-off tab 21 and the front end 60 of the syringe barrel 50. In FIG. 11, the needle shield/needle guard device 20 is attached in the extended lock position 36 on the front end 60 of the syringe barrel 50 and in that position the needle shield/needle guard device 20 covers the needle 53 which is permanently attached to the needle hub 52. FIG. 13 illustrates the detail of how the needle shield/needle guard device 20 (FIG. 11) is attached onto the front end 60 (FIG. 11) of the syringe barrel 50. This attachment occurs by sliding the bottom end 29 (FIG. 13) of the internal protrusion 27 over the funneled lead-in sloping groove 30, until as illustrated in FIG. 13 the internal protrusion 27 engages the retaining walls 33, 34 and 35 and the bottom end 29 of the internal protrusion 27 slip-fits into the extended lock position 36. The engagement of these aforementioned parts in (FIG. 13) provides a positive locking means for the needle shield/needle guard device 20 onto the front end 60 (FIG. 11) of the syringe barrel 50 and thereby prevents forward, backward, and counterclockwise movement of the needle shield/needle guard device 20 in relation to the front end 60 of the syringe barrel 50. In FIG. 11, pulling up on the handle 22 of the pull-off tab 21 will remove the pull-off tab 21 from the annular weakend zone 25 of attachment to the cylindrical housing 26, which creates an aperture 19 in the proximal part of the cylindrical housing 26.

In FIG. 12, the cylindrical housing 26 with the pull-off tab 21 removed, is shown in the retracted lock position 43 on the front end 60 of the syringe barrel 50, which uncovers the needle 53 permanently attached to the needle hub 52. The cylindrical housing 26 is placed in the retracted lock position 43 on the front end 60 of the syringe barrel 50 (see FIG. 3) by first sliding the internal protrusion 27 horizontally out of the extended lock position 36, over the constricting bead of the horizontal groove 37 into the horizontal groove 38, where the internal protrusion 27 is retained inside the horizontal groove 38 by the retaining wall 33. The internal protrusion 27 can slide from the horizontal groove 38 into the junction 40 and then into the longitudinal groove 39 where it can pass over the constricting bead of the longitudinal groove 42 to slip-fit into the retracted lock position 43. FIG. 14 illustrates a longitudinal sectional view of the bottom 29 of the internal protrusion 27 located in the retracted lock position 43. It is noteworthy that the retaining wall 35, which positively locks the internal protrusion 27 preventing its backward movement in relation to the front end 60 of the syringe barrel 50, and the horizontal groove 38, which directs the movement of the internal protrusion horizontally prior to its retraction into the longitudinal groove 39, provide safeguards to prevent the unintentional retraction of the cylindrical housing 26 in relation to the front end 60 of the syringe barrel 50. These safeguards prevent the unintentional retraction of the cylindrical housing 26 with the subsequent inadvertent exposure of the needle 53.

In this invention, the needle shield/needle guard device 20 is positively locked onto the front end 60 of the syringe barrel 50 where it encloses and thereby prevents contamination of a sterile needle 53 which is permanently attached to the front end of the syringe barrel 60. Once the pull-off tab 21 has been removed from the cylindrical housing 26 of the needle shield/needle guard device 20, the operator of this device can move the cylindrical housing 26 from the extended lock position 36 to the retracted lock position 43 on the front end 60 of the syringe barrel or vice versa. These maneuvers occur by first removing the pull-off tab 21 from the cylindrical housing 26 and then horizontally rotating the cylindrical housing 26 so that the internal protrusion 27 of the cylindrical housing 26 can be moved from the extended lock position 36 along the horizontal groove 38 to the longitudinal groove 39 and then into the retracted lock position 43, permitting retraction of the cylindrical housing 26 on the front end 60 of the syringe barrel 50, thereby un-covering the sterile needle 53. The cylindrical housing 26 can be moved back to the extended lock position 36 on the front end 60 of the syringe barrel 50 by reversing the movement of the internal protrusion 27 of the cylindrical housing 26 proximally along the longitudinal groove 39 into the horizontal groove 38 and then into the extended lock position 36, thereby re-covering the needle 53. The translucent material of the cylindrical housing 26 permits the user to clearly read the volumetric calibrations 51 on the surface of the syringe barrel 50 when the cylindrical housing 26 is moved over the front end 60 of the syringe barrel.

It is to be understood that, if necessary, other positive locks can be added to the groove system 61 to ensure the engagement of the internal protrusion 27 within the groove system 61. This can be accomplished in accordance with the same principles of the positive locking of the internal protrusion 27 in the extended lock position 36 to prevent forward, backward and counterclockwise movement of the needle shield/needle guard device 20 in relation to the front end 60 of the syringe barrel 50.

It is to be understood that the form of the invention herewith shown and described is to be taken as a preferred embodiment. Various changes may be made in the shape, size, and arrangement of parts, for example: equivalent elements may be substituted for those illustrated and described herein, parts may be reversed and certain features of the invention may be utilized independently of the use of other features, all without departing from the spirit or scope of the invention as defined in the subjoining claims.

We claim:

1. A combination needle shield/needle guard device which is positively locked onto a hypodermic syringe with a permanently attached needle;

said hypodermic syringe comprised of a syringe barrel with needle hub which is an integral part of front end of said syringe barrel;

said hypodermic needle permanently attached to said needle hub on front end of said syringe barrel;

said hypodermic syringe comprised of said syringe barrel with piston, said piston sliding inside said syringe barrel, providing means to force liquid medicament inside said syringe barrel through opening of said needle;

said needle shield/needle guard device comprising a hollow cylindrical housing which is sealed at its proximal end on weakend annular zone with an integral pull-off tab, said cylindrical housing with an internal protrusion located on distal inner wall of said cylindrical housing;

means for positive locking of said needle shield/needle guard device onto groove system on front end of said syringe barrel, said means preventing forward, backward and counterclockwise rotation of said needle shield/needle guard device in relation to front end of said syringe barrel;

means for said needle shield/needle guard device as needle shield to enclose said sterile needle which is permanently attached to said needle hub of said hypodermic syringe barrel;

means for aperture formation on proximal end of said needle shield/needle guard device;

means to prevent direct retraction of said cylindrical housing from extended lock position to retracted lock position;

means for said cylindrical housing of needle shield/needle guard device as said needle guard which can retract in relation to said syringe barrel, such that said cylindrical housing with said aperture can be moved from said extended lock position to said retracted lock position, uncovering said needle with said cylindrical housing;

means for said cylindrical housing of needle shield/needle guard device as said needle guard which can extend in relation to said syringe barrel, such that said cylindrical housing can be moved from said retracted lock position to said extended lock position, re-covering said needle with said cylindrical housing from behind the needle point of said needle;

means for said cylindrical housing as said needle guard to retract and extend ad-finitum in relation to said syringe barrel;

means for visibility of volumetric calibrations on said syringe barrel when said cylindrical housing has moved intos aid retracted lock position on said syringe barrel.

2. The invention as set forth in claim 1 with said means for positive locking said needle shield/needle guard device onto front end of said syringe barrel which prevents the forward, backward and counterclockwise rotation of said needle shield/needle guard device in relation to front end of said syringe barrel, said means for said positive lock comrising said internal protrusion of said cylindrical housing of needle shield/needle guard device which can slide onto funneled lead-in sloping groove on front end of said syringe barrel, until said internal protrusion slip-fits complementarily into positively locking retaining walls of said extended lock position.

3. The invention as set forth in claim 1, and particularly when said needle shield/needle guard device has been positively locked onto front end of said syringe barrel into said extended lock position, wherein said needle shield/needle guard device is provided with means as said needle shield to enclose said sterile needle permanently attached to said syringe barrel, said means comprising said hollow cylindrical housing of needle shield/needle guard device which is sealed at its proximal end by said pull-off tab integrally attached at the annular weakened zone on the proximal end of said cylindrical housing.

4. The invention as set forth in claim 3 with means for aperture formation, said means comprising said integral pull-off tab attached at said annular weakened zone on said proximal end of said cylindrical housing, such that said pull-off tab cab be removed from said annular weakened zone.

5. The invention as set forth in claim 1 with means to prevent direct retraction of said cylindrical housing from said extended lock position directly into longitudinal groove and then into said retracted lock position, said means comprising said internal protrusion of said cylindrical housing slip-fitting complementarily into said positive locking retaining walls of said extended lock position and said groove system with said internal protrusion of said cylindrical housing moving intially into horizontal groove prior to movement of said internal protrusion into said longitudinal groove and then into said retracted lock position.

6. The invention as set forth in claim 1 with said cylindrical housing of needle shield/needle guard device as said needle guard which is responsive to retraction movement in relation to said syringe barrel, and more particularly with said pull-off tab removed from said cylindrical housing, such that said internal protrusion of said cylindrical housing can move in said groove system from said extended lock position over constricting bead to said horizontal groove, then to said longitudinal groove into said retracted lock position, providing means for said cylindrical housing to move from said extended lock position to said retracted lock position, uncovering said needle enclosed by said cylindrical housing.

7. The invention as set forth in claim 1 with said cylindrical housing of needle shield/needle guard device as said needle guard, in which said cylindrical housing is in said retracted lock position on said syringe barrel, with said cylindrical housing responsive to extension movement in relation to said syringe barrel, such that said internal protrusion of said cylindrical housing can move in said groove system from said retracted lock position to said longitudinal groove to said horizontal groove over said constricting bead to said extended lock position, providing means for said cylindrical housing to move from said retracted lock position to said extended lock position, re-covering said needle with said cylindrical housing from behind said needle point of said needle.

8. The invention as set forth in claim 1 with a means for said cylindrical housing of said needle shield/needle guard device as a needle guard to retract, uncovering said needle, and re-extend, re-covering said needle, ad-finitum in relation to said syringe barrel, said means comprising said groove system with no positive locking retaining walls preventing the retraction movement of said internal protrusion of cylindrical housing from said extended lock position to said retracted lock position and no positive locking retaining walls preventing the extension movement of said internal protrusion of cylindrical housing from said retracted lock position to said extended lock position.

9. The invention as set forth in claim 1 with said cylindrical housing of needle shield/needle guard device comprised of a translucent material to provide means for visibility of volumetric calibrations on said syringe barrel when said cylindrical housing has moved into said retracted lock position on said syringe barrel.

* * * * *